(12) United States Patent
Weiner

(10) Patent No.: US 9,905,114 B2
(45) Date of Patent: Feb. 27, 2018

(54) HYGIENE MONITORING SYSTEM AND METHODS THEREOF

(71) Applicant: Brian C. Weiner, Morganville, NJ (US)

(72) Inventor: Brian C. Weiner, Morganville, NJ (US)

( * ) Notice: Subject to any disclaimer, the term of this patent is extended or adjusted under 35 U.S.C. 154(b) by 46 days.

(21) Appl. No.: 14/047,710

(22) Filed: Oct. 7, 2013

(65) Prior Publication Data

US 2014/0104062 A1    Apr. 17, 2014

Related U.S. Application Data

(60) Provisional application No. 61/710,731, filed on Oct. 7, 2012, provisional application No. 61/883,406, filed on Sep. 27, 2013.

(51) Int. Cl.
*G08B 23/00* (2006.01)
*G08B 21/24* (2006.01)
*G06Q 10/06* (2012.01)
*G07C 11/00* (2006.01)
(Continued)

(52) U.S. Cl.
CPC .......... *G08B 21/245* (2013.01); *A47K 5/1217* (2013.01); *A61L 2202/14* (2013.01); *G06Q 10/0635* (2013.01); *G06Q 10/06398* (2013.01); *G06Q 10/063114* (2013.01); *G07C 1/10* (2013.01); *G07C 11/00* (2013.01)

(58) Field of Classification Search
CPC .................................................. G08B 21/245
USPC ...................................................... 340/573.1
See application file for complete search history.

(56) References Cited

U.S. PATENT DOCUMENTS 6,038,331 A * 3/2000 Johnson ............. G06K 9/00375
                                                                    134/113
7,375,640 B1 * 5/2008 Plost .................... A47K 5/1217
                                                                    340/500
(Continued)

FOREIGN PATENT DOCUMENTS

WO    WO2010141689    12/2010

OTHER PUBLICATIONS

Form PCT/ISA/220, "Notification of Transmittal of the International Search Report and the Written Opinion of the International Searching Authority", Mailed Jul. 17, 2014 for PCT/US2013/063716, 2 Pgs.

(Continued)

*Primary Examiner* — Naomi Small
(74) *Attorney, Agent, or Firm* — Michael P. Kochka, Esq.

(57) ABSTRACT

A computer-implemented method and system for monitoring hygiene compliance is provided. In one embodiment, a computer-implemented method for monitoring hygiene compliance may include at a server having one or more processors and memory storing one or more programs for execution by the one or more processors: receiving hygiene data from a hygiene monitoring member, the hygiene data indicating the dates and times a user used a hygiene improvement apparatus and the length of time the user used the hygiene improvement apparatus; comparing the hygiene data with a hygiene protocol; determining if the hygiene data conforms to the hygiene protocol; generating an alert if the hygiene data does not conform to the hygiene protocol; and storing the hygiene data in a database.

11 Claims, 5 Drawing Sheets

(51) Int. Cl.
*G07C 1/10* (2006.01)
*A47K 5/12* (2006.01)

(56) References Cited

U.S. PATENT DOCUMENTS

| | | | | |
|---|---|---|---|---|
| 7,551,092 | B1* | 6/2009 | Henry | G08B 21/245 340/286.07 |
| 7,782,214 | B1* | 8/2010 | Lynn | G08B 21/245 340/540 |
| 7,819,136 | B1 | 10/2010 | Eddy | |
| 7,952,484 | B2 | 5/2011 | Lynn | |
| 8,040,245 | B2 | 10/2011 | Koblasz | |
| 8,294,585 | B2 | 10/2012 | Barnhill | |
| 8,558,660 | B2 | 10/2013 | Nix et al. | |
| 2003/0197122 | A1* | 10/2003 | Faiola | A61L 2/28 250/302 |
| 2006/0171843 | A1* | 8/2006 | Spears | A61L 2/0082 422/28 |
| 2006/0273915 | A1* | 12/2006 | Snodgrass | G08B 21/245 340/573.1 |
| 2008/0098424 | A1* | 4/2008 | Johnson | H04N 7/16 725/37 |
| 2009/0224924 | A1* | 9/2009 | Thorp | G08B 21/245 340/573.1 |
| 2009/0267776 | A1* | 10/2009 | Glenn | G08B 21/245 340/573.1 |
| 2010/0328076 | A1* | 12/2010 | Kyle | G06F 19/327 340/573.1 |
| 2010/0328443 | A1* | 12/2010 | Lynam | G06F 19/327 348/77 |
| 2011/0169646 | A1 | 7/2011 | Raichnan | |
| 2011/0227740 | A1* | 9/2011 | Wohltjen | G06F 19/327 340/573.1 |
| 2011/0316703 | A1 | 12/2011 | Butler et al. | |
| 2012/0062382 | A1* | 3/2012 | Taneff | G08B 21/245 340/573.1 |
| 2012/0075464 | A1 | 3/2012 | Derenne | |
| 2012/0212344 | A1* | 8/2012 | Forsberg | G08B 3/10 340/573.1 |
| 2012/0237919 | A1* | 9/2012 | Kelly | G09B 7/00 434/362 |

OTHER PUBLICATIONS

Form PCT/ISA/210, "International Search Report", Mailed Jul. 17, 2014 for PCT/US2013/063716, 3 Pgs.
Form PCT/ISA/237, "Written Opinion of the International Searching Authority", Mailed Jul. 17, 2014 for PCT/US2013/063716, 6 Pgs.

* cited by examiner

HYGIENE MONITORING SYSTEM AND METHODS THEREOF

CROSS-REFERENCE TO RELATED APPLICATIONS

The present application claims priority to U.S. Provisional Patent Application Ser. No. 61/710,731 entitled "Gimme 20," filed Oct. 7, 2012, and claims priority to U.S. Provisional Patent Application Ser. No. 61/883,406 entitled "HYGIENE MONITORING SYSTEM AND METHODS THEREOF," filed Sep. 27, 2013, the disclosures of which are incorporated herein by reference in their entireties.

BACKGROUND

Field of the Invention

Embodiments of the present invention generally relate to a hygiene monitoring system and methods thereof. More specifically, embodiments of the present invention relate to hygiene monitoring system for monitoring compliance to predetermined protocols related to hygiene.

Description of the Related Art

Many hospital-acquired (nosocomial) and food-borne infections are caused when individuals fail to exercise proper hand hygiene techniques. Infections are prevalent in all service facilities including hospitals, healthcare facilities, restaurants, food preparation facilities, and the like. When individuals fail to exercise proper hand hygiene techniques, they are more likely to carry microorganisms, including bacteria, that may cause infection. To reduce the incidence of these infections, proper hand hygiene techniques have been studied and standard protocols have been developed to reduce the risk of these infections.

Hand hygiene protocols have been designed to reduce the carriage of potential pathogens on the hands and decrease the incidence of preventable healthcare or food preparation infections, leading to a reduction in morbidity and mortality. Hand hygiene protocols may include, for example, a requirement that a user must wash his or her hands for a specified amount of time before and after an event, such as patient or food contact. To improve hand hygiene protocol compliance rates for these users, a need exists for an improved hygiene monitoring system and methods thereof.

SUMMARY

Embodiments of the present invention generally relate to a hygiene monitoring system and methods thereof. In one embodiment, a computer-implemented method for monitoring hygiene compliance may comprise, at a server having one or more processors and memory storing one or more programs for execution by the one or more processors, receiving hygiene data from a hygiene monitoring member, the hygiene data indicating the dates and times a user used a hygiene improvement apparatus and the length of time the user used the hygiene improvement apparatus; comparing the hygiene data with a hygiene protocol; determining if the hygiene data conforms to the hygiene protocol; generating an alert if the hygiene data does not conform to the hygiene protocol; and storing the hygiene data in a database.

In another embodiment of the present disclosure, a computer-implemented method for monitoring hygiene compliance may comprise, at a client having one or more processors and memory storing one or more programs for execution by the one or more processors, collecting hygiene data indicating the dates and times a user used a hygiene improvement apparatus and the length of time the user used the hygiene improvement apparatus; comparing the hygiene data with a hygiene protocol; determining if the hygiene data conforms to the hygiene protocol; generating an alert if the hygiene data does not conform to the hygiene protocol; and transmitting hygiene data to a server for storage on a database.

In yet another embodiment of the present disclosure, a system is provided that may comprise at least one client, the client comprising one or more processors; and memory; wherein the at least one client is adapted to collect hygiene data indicating the dates and times a user used a hygiene improvement apparatus and the length of time the user used the hygiene improvement apparatus; compare the hygiene data with a hygiene protocol; determine if the hygiene data conforms to the hygiene protocol; generate an alert if the hygiene data does not conform to the hygiene protocol; and transmit hygiene data to a server for storage on a database.

BRIEF DESCRIPTION OF THE DRAWINGS

So the manner in which the above recited features of the present disclosure can be understood in detail, a more particular description of embodiments of the present disclosure, briefly summarized above, may be had by reference to embodiments, which are illustrated in the appended drawings. It is to be noted, however, the appended drawings illustrate only typical embodiments of embodiments encompassed within the scope of the present disclosure, and, therefore, are not to be considered limiting, for the present disclosure may admit to other equally effective embodiments, wherein.

Figure 1:
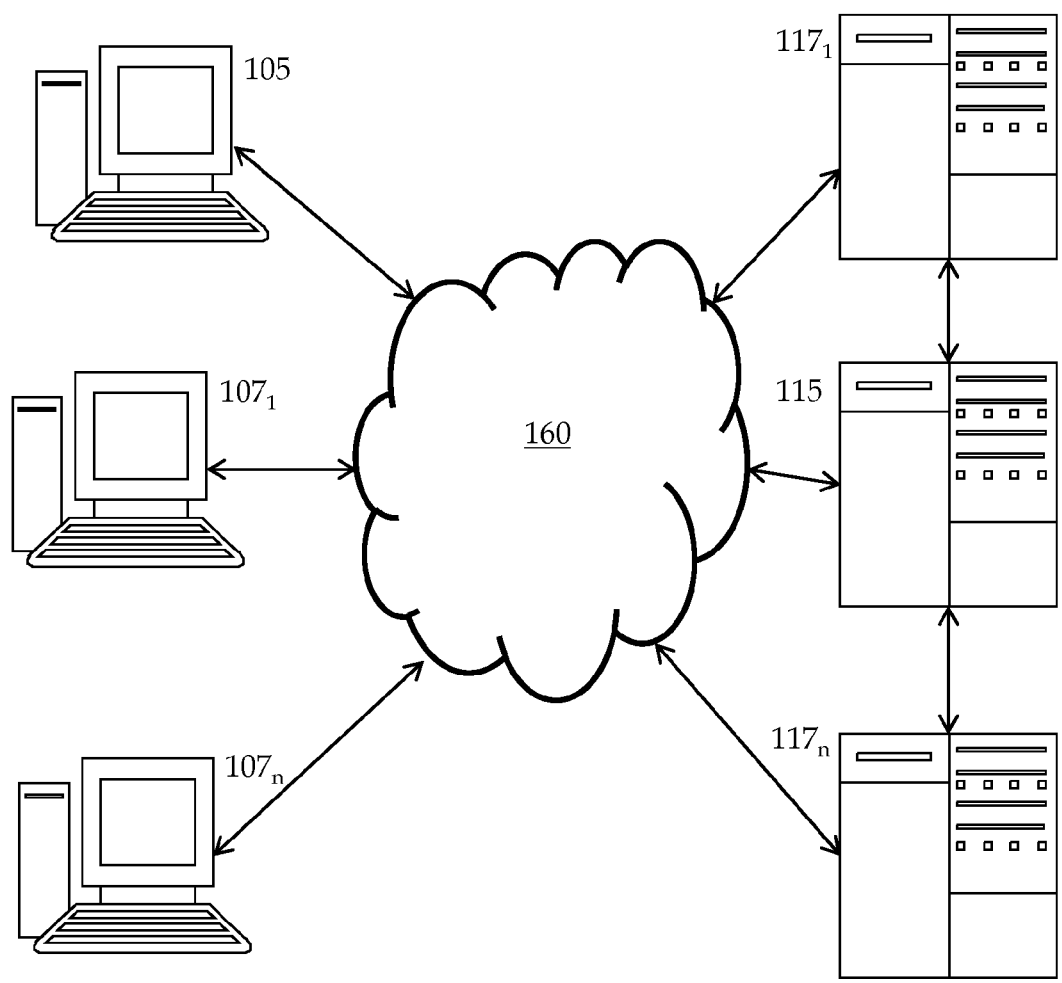
FIG. 1 depicts a block diagram of an exemplary hygiene monitoring system in accordance with embodiments of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

Embodiments of the present invention generally relate to a hygiene monitoring system and methods thereof. More specifically, embodiments of the present invention relate to hygiene monitoring system for monitoring compliance to predetermined protocols related to hygiene.

In the following detailed description, numerous specific details are set forth in order to provide a thorough understanding of exemplary embodiments or other examples described herein. However, it may be understood that these examples may be practiced without the specific details. In other instances, well-known methods, procedures, components and circuits have not been described in detail, so as to not obscure the following description. Further, the examples disclosed herein are for exemplary purposes only and other examples may be employed in lieu of, or in combination with, the examples disclosed. It should also be noted that the examples presented herein should not be construed as limiting of the scope of embodiments of the present disclosure, as other equally effective examples are possible and likely.

In accordance with certain embodiments of the present disclosure, methods disclosed herein may occur in "real-time." Real-time is utilized herein as meaning near-instantaneous, subject to minor delays caused by network transmission and computer processing functions, and able to support various input and output data streams.

FIG. 1 depicts a block diagram of an exemplary hygiene monitoring system 400 in accordance with embodiments of the present invention. In exemplary embodiments, the system 400 may be adapted to capture, transmit, analyze, filter, review, and/or information related to a hygiene process. For example, the system 400 may be adapted to collect data relating to compliance with a predetermined hygiene policy, such as a requirement for users to wash their hands for a predetermined length of time. In accordance with embodiments of the present invention, information may be collected and transmitted to a central repository.

In accordance with exemplary embodiments, the system 400 generally comprises at least a first client 105, generally in communication with a server 115 via a network 160. In some embodiments, the system 400 may comprise secondary clients $107_1$ and 107n. The clients may be in communication with the host server 115, generally through the network 160. In some embodiments, a client may comprise a hygiene monitoring apparatus, or the like. As is common in network-based business models, an administrator 110 may be responsible for providing and maintaining a website or interactive portal through which users of the system 400 may interact and execute the methodology and functionality disclosed in the embodiments of the present invention.

Methods in accordance with embodiments of the present invention may take place over the network 160, which may comprise a global computer network, for example, the internet. The communications functions described herein can be accomplished using any kind of wired and/or wireless computing network or communications means capable of transmitting data or signals, such as a wireless and/or wired computing network allowing communication via, for example, an 802.11 ("Wi-Fi") protocol, cellular data protocol (e.g., EDGE, CDMA, TDMA, GSM, LTE), and/or the like. Suitable examples include a packet-switched network, a local area network (LAN), wide area network (WAN), virtual private network (VPN), or any other means of transferring data. The network 160 may be a partial or full deployment of most any communication/computer network or link, including any of, any multiple of, any combination of or any combination of multiples of a public or private, terrestrial wireless or satellite, and wire-line networks or links. A single network 160 or multiple networks (not shown) that are communicatively coupled to one another can be used. It is contemplated that multiple networks of varying types can be connected together and utilized to facilitate the communications contemplated by the systems and elements described in this disclosure.

Although FIG. 1 depicts two secondary clients 1071 and 107n, it should be appreciated that "n" represents any number of clients feasible in accordance with embodiments of the present disclosure. For ease of reference, as used herein, the term "client" may refer to any one or all of the clients, 105, $107_1$, and 107n within the system 400. That is, in certain embodiments, multiple clients may perform the same or similar functions. For ease, one client 105 may be referred to herein, however in exemplary embodiments, more than one client 105 may be included in the system 400.

As used herein, the term "computer" may generally refer to any device that is capable of processing a signal or other information. Examples of computers include, without limitation, a personal computer, a portable computer, a handheld computer, a cellular phone, a smart phone, a digital tablet, a laptop computer, a netbook, an Internet appliance, a Personal Data Assistant (PDA), an application-specific integrated circuit (ASIC), a programmable logic array (PLA), a microcontroller, a digital logic controller, a digital signal processor (DSP), or the like, or may generally include a general purpose computer, as discussed below with respect to FIG. 2. A computer may include software in the form of programmable code, micro code, and or firmware or other hardware embedded logic and may include multiple processors which operate in parallel. The processing performed by a computer may be distributed among multiple separate devices, and the term computer encompasses all such devices when configured to perform in accordance with the disclosed embodiments.

The client 105 may generally comprise a hygiene monitoring apparatus, a communications device, a computer, and/or the like. In a basic exemplary embodiment, within the system 400, the client 105 may be capable of transmitting data to and from a host server 115. The host server 115 may host an accessible data portal (e.g., a website or the like). The accessible data portal, which may be accessible to the client 105, may communicate with the client 105 through the network 160. The accessible data portal may comprise any number of security measures to provide a reasonably secure system, suitable for embodiments of the present disclosure. As examples, security may be provided by use of unique passwords, unique bar codes or QR codes, or by digital fingerprint technology. The accessible data portal may further comprise a graphical client interface (GUI) through which a client 105 may access the server 115.

The system may also comprise secondary servers $117_1$ and 117n. Although two secondary servers $117_1$ and 117n are depicted in FIG. 1, it should be appreciated that "n" represents any number of servers feasible in accordance with embodiments of the present disclosure. For ease of reference, as used herein, the term "server" may refer to any one or all of the servers, 115, $117_1$, and 117n within the system 400. That is, in certain embodiments, multiple servers may perform the same or similar functions.

The server 115 may also comprise a database or other sortable data storage memory to enable the system and methods disclosed herein. In many embodiments, the database may be any commercially available data storage database suitable for embodiments of the present disclosure. For example, in one embodiment, the database comprises at least one or more database management systems, such as any of an Oracle, DB2, Microsoft Access, Microsoft SQL Server, Postgres, MySQL, 4th Dimension, FileMaker, Alpha Five Database Management System, or the like. Often contained within the database is a plurality of data sets, each comprising specific data. A first data set may correlate to a first client 105, wherein a plurality of client-specific data is stored. The database may also include any number of subsequent data sets representing N clients, wherein N represents any number of clients practical for operation of embodiments of the present disclosure. In accordance with one embodiment of the present disclosure, any of the servers or clients may comprise a general purpose computer, for example, as shown in the form of a computer 210 depicted in FIG. 2.

Figure 2:
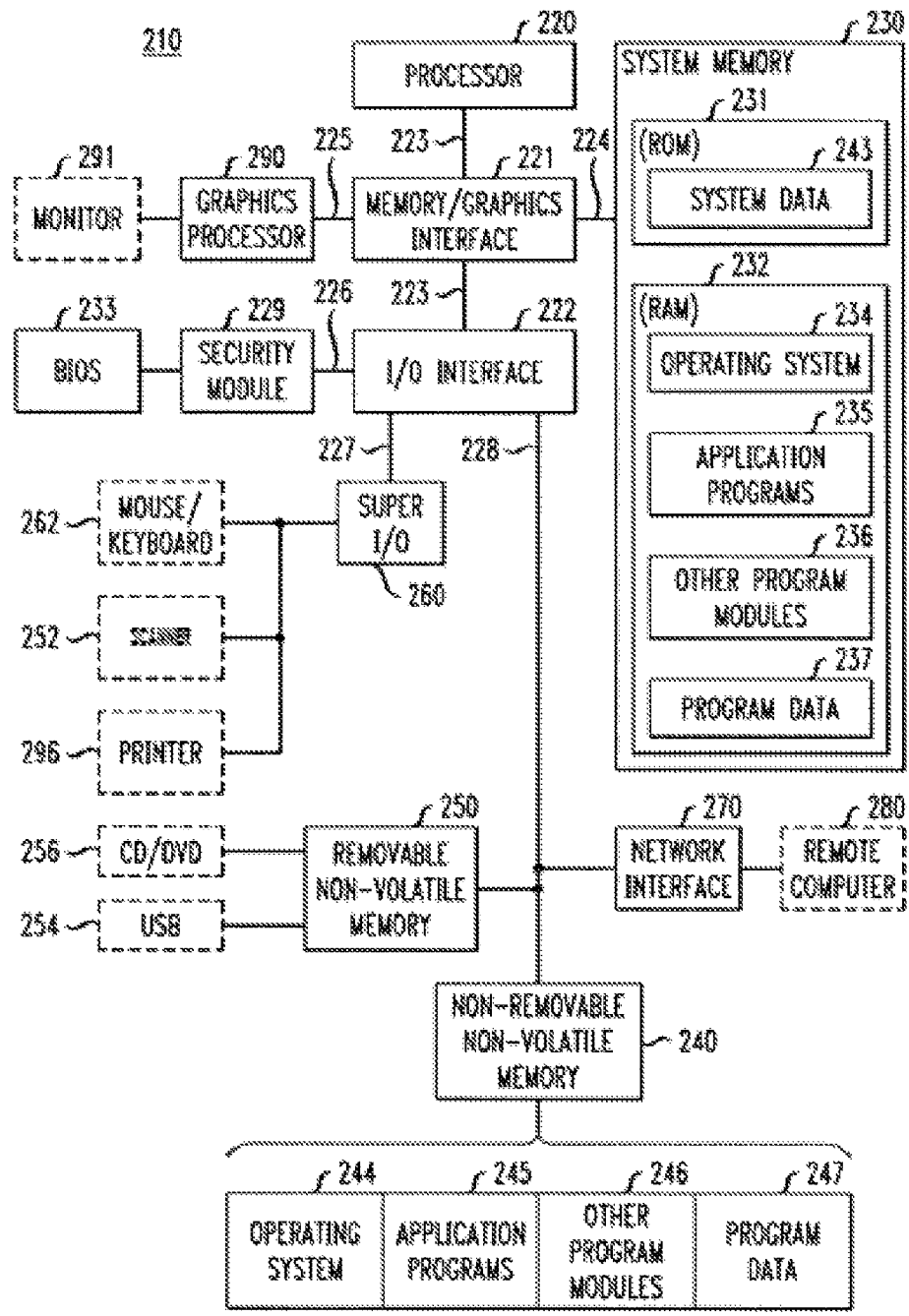
FIG. 2 depicts a block diagram of a general computer system in accordance with embodiments of the present invention.

FIG. 2 depicts a block diagram of a general computer system, which is capable of being used in connection with the system depicted in FIG. 1, in accordance with embodiments of the present disclosure. As appreciated by embodiments of the present disclosure, mobile devices, such as mobile hygiene monitors, mobile telephones, tablets, netbooks, or the like, may be utilized instead a general computer 210 for embodiments of the present disclosure. However, it is also appreciated there is a significant similarity in core components between a mobile device and a general computer 210. The following components are described for exemplary purposes only, and each component's mobile equivalent is also contemplated within embodiments of the present disclosure.

Components shown in dashed outline are not part of the computer 210, but are used to illustrate the exemplary embodiment of FIG. 2. Components of computer 210 may include, but are not limited to, a processor 220, a system memory 230, a memory/graphics interface 221, also known as a Northbridge chip, and an I/O interface 222, also known as a Southbridge chip. The system memory 230 and a graphics processor 290 may be coupled to the memory/graphics interface 221. A monitor 291 or other graphic output device may be coupled to the graphics processor 290.

A series of system busses may couple various system components including a high speed system bus 223 between the processor 220, the memory/graphics interface 221 and the I/O interface 222, a front-side bus 224 between the memory/graphics interface 221 and the system memory 230, and an advanced graphics processing (AGP) bus 225 between the memory/graphics interface 221 and the graphics processor 290. The system bus 223 may be any of several types of bus structures including, by way of example, and not limitation, such architectures include Industry Standard Architecture (ISA) bus, Micro Channel Architecture (MCA) bus and Enhanced ISA (EISA) bus. As system architectures evolve, other bus architectures and chip sets may be used but often generally follow this pattern. For example, companies such as Intel and AMD support the Intel Hub Architecture (IHA) and the Hypertransport architecture, respectively.

The computer 210 typically includes a variety of computer readable media. Computer readable media can be any available media that can be accessed by computer 210 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EPROM, flash memory or other memory technology, CD-ROM, digital versatile disks (DVD), blue-ray or other optical disk storage, magnetic cassettes, magnetic tape, magnetic disk storage or other magnetic storage devices, or any other medium which can be used to store the desired information and which can be accessed by computer 210. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 230 includes computer storage media in the form of volatile and/or nonvolatile memory such as read only memory (ROM) 231 and random access memory (RAM) 232. The system ROM 231 may contain permanent system data 243, such as identification information. In some embodiments, a basic input/output system (BIOS) may also be stored in system ROM 231. RAM 232 typically contains data and/or program modules that are immediately accessible to and/or presently being operated on by processor 220. By way of example, and not limitation, FIG. 2 illustrates operating system 234, application programs 235, other program modules 236, and program data 237.

The I/O interface 222 may couple the system bus 223 with a number of other busses 226, 227 and 228 that couple a variety of internal and external devices to the computer 210. A serial peripheral interface (SPI) bus 226 may connect to a basic input/output system (BIOS) memory 233 containing the basic routines that help to transfer information between elements within computer 210, such as during start-up. In some embodiments, a security module 229 may be incorporated to manage metering, billing, and enforcement of policies. The security module 229 may comprise any security technology suitable for embodiments disclosed herein.

A super input/output chip 260 may be used to connect to a number of peripherals, such as a scanner 252, keyboard/mouse 262, and printer 296, as examples. The super I/O chip 260 may be connected to the I/O interface 222 with a low pin count (LPC) bus, in some embodiments. The super I/O chip 260 is widely available in the commercial marketplace. In one embodiment, bus 228 may be a Peripheral Component Interconnect (PCI) bus, or a variation thereof, may be used to connect higher speed peripherals to the I/O interface 222. A PCI bus may also be known as a Mezzanine bus. Variations of the PCI bus include the Peripheral Component Interconnect-Express (PCI-E) and the Peripheral Component Interconnect-Extended (PCI-X) busses, the former having a serial interface and the latter being a backward compatible parallel interface. In other embodiments, bus 228 may be an advanced technology attachment (ATA) bus, in the form of a serial ATA bus (SATA) or parallel ATA (PATA).

The computer 210 may also include other removable/non-removable, volatile/nonvolatile computer storage media. By way of example only, FIG. 2 illustrates a hard disk drive 240 that reads from or writes to non-removable, nonvolatile magnetic media. Removable media, such as a universal serial bus (USB) memory 254 or CD/DVD drive 256 may be connected to the PCI bus 228 directly or through an interface 250. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. In one exemplary configuration, the data on media will be accessed by digital fingerprint control.

The drives and their associated computer storage media discussed above and illustrated in FIG. 2, provide storage of computer readable instructions, data structures, program modules and other data for the computer 210. In FIG. 2, for example, hard disk drive 240 is illustrated as storing operating system 244, application programs 245, other program modules 246, and program data 247. Note that these components can either be the same as or different from operating system 234, application programs 235, other program modules 236, and program data 237. Operating system 244, application programs 245, other program modules 246, and program data 247 are given different numbers here to illustrate that, at a minimum, they are different copies. A client may enter commands and information into the computer 210 through input devices such as a mouse/keyboard 262 or other input device combination. Other input devices (not shown) may include a microphone, joystick, game pad, satellite dish, camera, radio-frequency identification (RFID) transmitter/receiver/reader, fingerprint scanner, retina scanner, wireless transmitter/receiver, barcode or QR scanner, Bluetooth transmitter/receiver, scanner, and/or the like. These and other input devices are often connected to the processor 220 through one of the I/O interface busses, such as the SPI 226, the LPC 227, or the PCI 228, but other busses may be used. In some embodiments, other devices may be coupled to parallel ports, infrared interfaces, game ports, and the like (not depicted), vithe super I/O chip 260.

The computer 210 may operate in a networked environment using logical connections to one or more remote computers, such as a remote computer 280 via a network interface controller (NIC) 270, or the like. The remote computer 280 may be a personal computer, a server, a router, a network PC, a peer device or other common network node, and typically includes many or all of the elements described above relative to the computer 210. The logical connection between the NIC 270 and the remote computer 280 depicted in FIG. 2 may include a local area network (LAN), a wide area network (WAN), or both, but may also include other networks. Such networking environments are commonplace in offices, enterprise-wide computer networks, intranets, and the Internet. In some embodiments, the network interface may use a modem (not depicted) when a broadband connection is not available or is not used. It may be appreciated that the network connection shown is exemplary and other means of establishing a communications link between the computers may be used.

Although the computer 210 of FIG. 2 is described as an exemplary computing device for various applications of embodiments of the present invention, it should be appreciated, a multitude of similar computing devices exist and are equally suitable for embodiments of the present invention. It is further understood by embodiments of the present invention, a computing device may comprise all of the elements disclosed in FIG. 2, or any combination of one or more of such elements, in order to perform the necessary functions of the embodiments of the present disclosure.

It is understood by embodiments of the present disclosure that a computer, such as the one depicted in FIG. 2, may be connected to a computer network or system. A computer network may include the Internet, a global computer network, a cloud network, an internal computer network, dedicated server networks, or the like.

Figure 3:
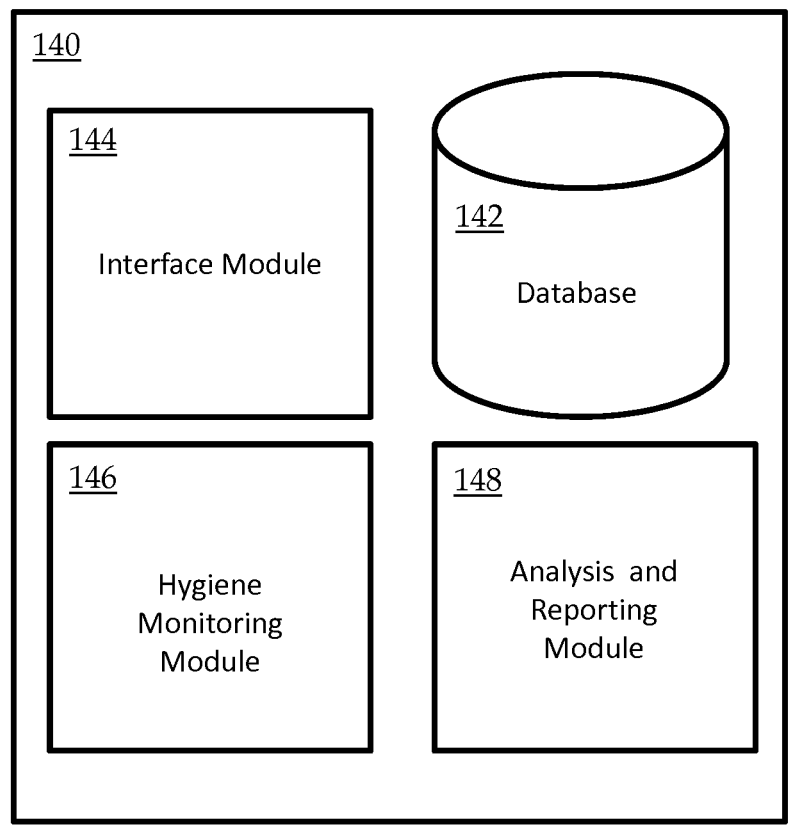
FIG. 3 depicts a block diagram of a hygiene monitoring system in accordance with embodiments of the present invention.

FIG. 3 depicts a block diagram of a hygiene monitoring system 140 in accordance with embodiments of the present invention. The hygiene monitoring system 140 may generally comprise computer executable software and/or instructions configured to perform the functionality of the systems and methods disclosed herein. The hygiene monitoring system 140 may be stored on a server, on a local computing device, on a mobile communications device, and/or the like. The hygiene monitoring system 140 may comprise a database 142, an interface module 144, a hygiene monitoring module 146, an analysis and reporting module 148, and/or the like. In accordance with exemplary embodiments of the present invention, any module may be merged and/or combined with any other module. In some embodiments, additional or fewer modules than those depicted in FIG. 3 may be included.

In exemplary embodiments, the hygiene monitoring system 140 may be configured to capture, analyze, and store all information related to a hygiene monitoring procedure. For example, the hygiene monitoring system 140 may be adapted to capture and store the amount of time a user spends washing his or her hands. In some embodiments, the hygiene monitoring system 140 may be configured to provide real-time or substantially real-time hand hygiene compliance information to users upon request, at predetermined intervals, upon the occurrence of an event, and/or the like. In exemplary embodiments, the term "user" may generally refer to any party provided with access to the systems and methods in accordance with embodiments of the present invention. For example, a user may comprise a healthcare provider, a patient, a food preparer, a member of a restaurant staff, and/or the like.

In exemplary embodiments, the interface module 144 may be adapted to provide the user with a means for interacting with the hygiene monitoring system 140. The interface module 144 may be adapted to present a graphical user interface (GUI) to the user, the GUI adapted to allow users to input, view, and interact with the hygiene monitoring system 140. In some embodiments, the interface module 144 may be adapted to present information to a user via a display on a computer, a tablet, a mobile device, a laptop, a touchscreen device, and/or the like. In one embodiment, the display may be integral with a soap dispenser, and/or the like. The interface module 144 may also be adapted to provide an opportunity to register a user account for accessing the hygiene monitoring system 140. In some embodiments, the interface module 144 may be adapted to display a countdown established by the hygiene monitoring module, or the like. For example, when the user initiates a hand washing procedure, the interface module 144 may be adapted display the time remaining for proper hand washing. For example, the time remaining for proper hand washing may be 20 seconds. The interface module 144 may be adapted to provide selected content related to a hygiene procedure, for example, a video demonstration of a hand washing technique in compliance with a hygiene protocol. In some embodiments, the interface module 144 may display information of interest to the user, such as local news, weather, sports information, hospital data, patient data, and/or the like.

In accordance with exemplary embodiments of the present invention, the interface module 144 may also allow a user to access hygiene data stored by the analysis and reporting module 148. The interface module 144 may be adapted to allow the user to run a report on the data contained in the database 142 with the analysis and reporting module 148. In some embodiments, a user may access hygiene data upon running a report request with the interface module 144. Hygiene data may comprise data relating to whether or not a user and/or group of users are in compliance with a hygiene protocol. For example, hygiene data may include the date, time, and duration of each time a user washed his or her hands. The interface module 144 may also be adapted to transmit and/or display alert messages to the user when a user is not in compliance with a hand washing module. An event that triggers an alert may comprise, for example, when a user has not washed his or her hands for a predetermined amount of time, for example, twenty seconds.

In exemplary embodiments, alerts may be presented to the user via a display on a computer or electronic device, via a text or SMS message, via an automated phone call, via email, via an auto-generated letter via postal mail. When an alert is generated, it may be sent to multiple parties. For example, if the analysis and reporting module 148 determines that a user has not washed his or her hands for a predetermined amount of time and an alert should be generated, an alert may be generated and sent via one or more communication means to the user and/or the user's supervisor.

In accordance with exemplary embodiments of the present invention, the hygiene monitoring module 146 may be adapted to receive data from a device, such as a hygiene monitor and/or the like. For example, the hygiene monitoring module 146 may be adapted to receive and save the amount of time a user washes his or her hands in a database 142. In accordance with exemplary embodiments, the database 142 may be adapted to store all hygiene data. In accordance with exemplary embodiments, the analysis and reporting module 148 may be adapted to analyze hygiene data collected by the hygiene monitoring module. The analysis and reporting module 148 may be adapted to find and/or identify data that indicates noncompliance with a hygiene protocol, or the like.

The analysis and reporting module 148 may be adapted to flag and identify users and/or groups of users that have not complied with the hand washing protocol. The analysis and reporting module 148 may compare the collected hygiene data with hygiene protocol data. Hygiene protocol data may generally be set by medical practice standards boards, by healthcare providers, and/or the like. If the collected hygiene data does not comply with a hygiene protocol, an alert may be generated. When a user has not complied with a hand washing protocol, the analysis and reporting module 148 may be adapted to notify the user and/or administrator via the interface module 144. The analysis and reporting module 148 may also be adapted to generate reports and/or alerts comprising a summary of all users' compliance with hand washing protocols. The reports and/or alerts may be transmitted and/or displayed to the user via text or SMS message, mobile communication device, email, postal mail, a report generated on the display of a computing device, and/or the like.

In some embodiments, a hygiene monitoring system 140 may be adapted to collapse indications for hand hygiene. For example, a health care worker following World Health Organization ("WHO") recommendations may be required to perform hand hygiene upon walking into a room (WHO moment 1) and again before performing a procedure or handling the patient (WHO moments 2, 3). The system 140 may consolidate and/or collapse these moments into one hand hygiene episode to cover all these indications. In some embodiments, they stem 140 may be adapted to allow a user, such as a healthcare professional, the opportunity to appropriately attest to the collapsing of these hand hygiene moments into a single hand hygiene episode. In some embodiments, the attestation would occur by the health care worker identifying him or herself, for example, by placing a fingerprint incorporated into an identification card worn in the hospital setting. In some embodiments, the attestation would be recorded remotely by a server and subject to analysis by automated or manual review.

In some embodiments, healthcare and/or food preparation services may be complex and hygiene protocols may not fit every possible scenario. In such cases, a health care professional would be able to override the system 140 manually. In some embodiments, a system 140 may provide visual, audio, and/or tactile feedback to patients, administrators, healthcare providers, and/or the like, that user has complied with hand hygiene protocols. In some embodiments, the system 140 may provide feedback wirelessly to a user's identification card or identification means, providing a signal, such as a green indication, confirming compliance with hand hygiene and signal, such as a red indication, when hand hygiene is not completed. In some embodiments, the system 140 may provide feedback wirelessly to a second location or user, such as a patient's room or patient care area, that all health care workers in the area are compliant, or an indication if any are noncompliant. In some embodiments, the system 140 may identify and display the health care workers or the like in compliance and not in compliance with a hygiene protocol.

In some embodiments, as part of the beginning of the work day, or prior to critical procedures, the system 140 may be adapted to allow a health care worker, or the like, to sign into the system and may present them with tasks that test memory and mental and/or physical agility. This would be done to show that health care workers are alert, not drowsy or tired, not intoxicated and ready for work, or the like. As an example, a health care worker could be prompted to enter "serial 7s", a countdown from 100 by 7s, measured in time, to assess mental agility.

Figure 4:
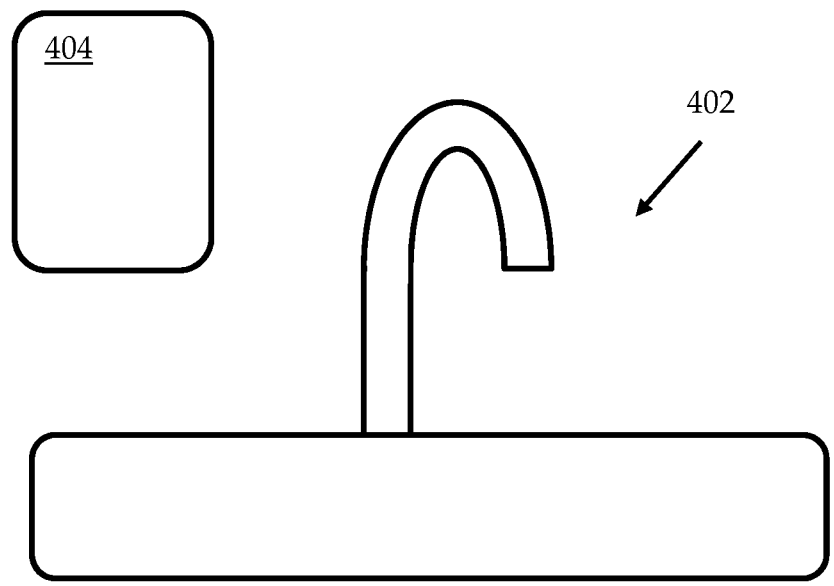
FIG. 4 depicts an exemplary hygiene monitoring system in accordance with embodiments of the present invention.

FIG. 4 depicts an exemplary hygiene monitoring system 400 in accordance with embodiments of the present invention. In exemplary embodiments, a hygiene monitoring system 400 may comprise a monitor 404 and a hygiene improvement apparatus 402. The monitor 404 may be adapted to monitor a user's compliance, or lack of compliance, with a predetermined protocol for improvement of hygiene. For example 400, an administrator may establish that twenty seconds is the required amount of time an individual must wash their hands before proceeding to another task. In this exemplary embodiment, the monitor 404 may be adapted to determine if a user has washed his or her hands for over the threshold amount of time.

A hygiene monitoring system 400 in accordance with embodiments of the present invention may be beneficial for industries that require good hygiene practices to prevent the spread of infectious disease, or the like. For example, a hygiene monitoring system 400 may be beneficial to a healthcare facility in assisting to preserve the health of patients, healthcare providers, staff, and/or the like. A hygiene monitoring system 400 may also be beneficial to a food or beverage provider, processor, and/or the like, in assisting to preserve the health of its customers, employees, factory workers, cooks, wait staff, and/or the like. The hygiene monitoring system or any of its components may also be beneficial in any area where hygiene is required, as a domestic bathrooms or kitchens, general office bathrooms and lunch rooms, factory bathrooms and lunchrooms. The hygiene improvement apparatus 402 may comprise any device adapted to allow a user to employ a hygiene practice. For example, a hygiene improvement apparatus 402 may comprise a sink, a shower, an isolation apparatus, protective clothing, sterilization instruments, bandaging, medical waste disposal receptacles, disinfection instruments and appliances, and/or the like. By way of example, a sink is depicted in FIG. 4. For ease, a sink is referred to herein to describe an example hygiene improvement apparatus 402.

Any hygiene improvement apparatus 402 that may be monitored with a hygiene monitor 404 is contemplated by and within embodiments of the present invention, however.

In exemplary embodiments, the monitor 404 may comprise a timer that may be set off at the time of initiation of a procedure to improve hygiene. For example, when a sink 402 is turned on, the monitor 404 may begin the timer. In some embodiments, the monitor 404 may automatically initiate the timer. In alternative embodiments, the monitor 404 may be manually activated when the sink is turned on. For example, the monitor 404 may comprise a component either integral with the sink 402 or located in proximity to the sink 402 that detects when the faucet of the sink has been turned on by detecting the presence of water, by detecting the sink valves have been opened, and/or the like.

Although the monitor 404 is depicted in FIG. 4 as a separate apparatus, the monitor 404 may be integrated within a portion of the sink 402, or the like. For example, the monitor 404 may be integrated within the spout of the sink 402. When used in close proximity to a sink 402, the monitor 404 may comprise water-resistant, water repellant, and/or waterproof materials, and may be adapted to substantially prevent damage caused by water or other liquids. In some embodiments, the monitor 404 may be mounted, attached, or otherwise supported in proximity to the sink 402, a soap dispenser, and/or the like. In some embodiments, the monitor 404 may be adapted to monitor the amount of soap, or the like, that has been dispensed from a dispenser, or the like. This monitor may be adapted to notify maintenance staff when soap or hand hygiene materials are nearly exhausted and need replenishment.

In exemplary embodiments, the monitor 404 may provide and/or display an indication of the proper amount of time for scrubbing of hands to provide effective hand washing. In some embodiments, the monitor 404 may be provided with a default countdown time. For example, a default countdown time may be 20, 30, or 45 seconds, or the like. The default time may be adjusted as required by the needs at a specific location. The system 400 may provide an audio signal when hand washing starts and when it is completed. The system 400 may provide a video signal and a countdown of seconds until the completion of the minimum time for hand washing.

In some embodiments, the monitor 404 may be adapted to display information, audio, video, text, images, and/or the like that can be specified by a client. For example, a default video may display and/or demonstrate one or more proper hand washing techniques. The monitor 404 may also be adapted to display real time data, such as stock prices, sport scores, weather information, general advertisements, targeted advertisements, medical educational information, treatment option information, pharmaceutical product information, the number of patients in a hospital or census, the time, and/or the like. The monitor 404 may be adapted to display custom content set up by an administrator. In some embodiments, the custom content may depend upon a compliance rating of the user. For example, if a user has a compliance rating below a selected percentage, a training video, or the like, may be displayed to the user. In some embodiments, a user's compliance rating may comprise a percentage that the user complies with a hand hygiene protocol. In some embodiments, the user may be presented with targeted advertisements based on a user profile set up by the user and/or the administrator. For example, a specialist medical professional may be presented with targeted advertisements related to his or her specialty by the monitor 404.

The monitor 404 may be durable, appropriate for installation in medical locations, food preparation locations, locations wherein heavy use is anticipated, and/or the like. The monitor 404 may be in compliance with safety standards. For example, the monitor 404 may in compliance with the Underwriters Laboratories (UL) standard, and the European Exonomic Area (EEA) CE standards, and/or the like. The monitor 404 may comprise one or more elements that are cleanable and sanatizable. The monitor 404 may be adapted to be hung, mounted, placed, or otherwise displayed near existing sinks, preferably near existing soap dispensers.

In one embodiment, the monitor 404 may be incorporated in the soap dispenser and/or the faucet controlling the water for hand washing. The monitor 404 may comprise a power source. For example, the monitor 404 may be battery powered, and/or solar cell operated, to avoid the need to operate the device on routine grid electric power. In some embodiments, the monitor 404 may be powered by AC power and/or may comprise an AC connection for backup purposes if a battery fails or loses its charge. In some embodiments, the monitor 404 may be wired into the information grid and/or power grid of an end user. In exemplary embodiments, the monitor 404 system may be leased to one or more end users. As part of that lease, an administrator may be responsible for maintaining the functionality of the system 400, including replacement of batteries, maintenance, and/or the like, as needed.

In some embodiments, the monitor 404 may have a video display that may provide a countdown, and may provide other information relevant to the host institution in which the device is placed, or the like. Such information may comprise instructions in hand washing, for example, the 6 required poses for hand washing; other events to be promoted at the host institution; general information that is of interest, as a local weather report; advertising provided by the device supplier or the host institution, and/or the like. In some embodiments, the monitor 404 may connect to the Internet or an intranet wirelessly, to monitor battery life or to change or update information displayed on the device. The monitor 404 may be programmed and/or reprogrammed to update information displayed on the device, to change the number of seconds displayed for hand washing time, and/or to assess the battery life.

The monitor 404 may be adapted to identify the user. For example, the monitor 404 may allow a user to enter a unique identifying code into a keypad, touch screen, and/or the like. The monitor 404 may be adapted to identify a user by scanning a bar code, QR box, a radio frequency identification (RFID) tag on the individual's identification, digital fingerprint recognition and/or the like. The monitor 404 may be adapted to monitor the identified user's compliance with a hygiene protocol, for example, washing hands for a specified time period upon entering or exiting a particular area, at predetermined time intervals, at predetermined times, and/or the like. In some embodiments, every patient may have a unique identifier, such as a bar code, QR box, RFID, or the like, that may be added to existing identification cards. One or more rooms, instruments, and/or pieces of equipment may have similar identification by bar code, QR box or RFID, or the like. The monitor 404 may be communicatively coupled with a network for the collection, saving, and/or analysis of hygiene monitoring data.

The system 400 may provide ability to generate appropriately equipped identification cards on their sites. For example, the system 400 may comprise an ID or unique identifier generation means. The ID and/or unique identifier means may be coupled with a network and/or a central server for collecting and saving data related to each user of the system. For example, data related to each healthcare provider, each patient, each instrument, each room, each event, and/or the like may be collected and stored by the system 400. For every interaction between a healthcare provider and the monitor 404, a unique, time stamped, interaction number may be generated. This number may allow tracking of the hand hygiene episode, the patient, the healthcare provider, and may allow correlation with a specific patient care event. The number may be tracked by the monitor 404 system, and can also be sent to the healthcare provider and to the healthcare insurer, the hospital's data system and any other appropriately interested entity, for example, an accreditation agency. In some embodiments, specific incidents of infection may be tracked and a user that caused the infection may be identified. For example, when a patient experiences an infection and the patient has come into contact with a user that was not in compliance with a hand washing protocol within a period of time, the monitor 404 may indicate that it is likely the user caused the infection. In some embodiments, the monitor 404 may also track the amount of time a user spends on attending to a specific task to facilitate billing of the task.

The identification of an individual by the monitor 404 may allow the host institution to audit the location of hand washing, the timing of hand washing as related to some critical interaction, such as patient care, and or the like. The monitor 404 may perform audits of hand washing, or a remote server may audit hand washing and/or hygiene compliance data collected by the monitor 404. Hygiene audits performed by the system 400 may allow the host institution to better identify the causation of episodes of infection in the facility, and to track infections to specific individuals. The monitor 404 may comprise a camera to monitor hand washing skills. In some embodiments, the system 400 may compare the captured video of a user washing his or her hands with ideal hand washing techniques. For example, a computer vision program implemented in the system 400 may automate the monitoring of quality of hand washing skills.

A monitor 404 camera can be activated by the same action that sets off the hand washing timer or by other motion. The monitor 404 camera can be used to document that the worker under observation has properly used other infection control materials, such as gloves and gowns in hospital settings. The monitor 404 camera can either store the information in the device for later retrieval, or the information can be sent wirelessly via internet or intranet to a central server for analysis.

As the monitor 404 may have a way to identify individuals using the system 400, the monitor 404 can measure the time that an individual spends attending to a specific task or patient in a healthcare setting. This time measurement can facilitate billing activities in which time is measured, and quality assurance activities, and/or the like. When the monitor 404 is strategically located, the interaction of the monitored individual may be documented by the camera in the device, for facilitation of billing activities, quality assurance activities and tracking specific infections.

When the monitor 404 is communicating with a central server, real time assessments of the observed washing activity or other monitored activity may be made. The central server may comprise monitoring software to alert supervisors or interested individuals of lack of compliance with washing or other protocols, or other deviations from expected outcomes. In some embodiments, the central server may initiate automated contact with the responsible individual in the event of lack of compliance. The central server may initiate awards for individuals with predefined levels of compliance with host institution protocols. The award may be in the form of a coupon that may be printed by the monitoring device, or may be generated on the screen of the device for scanning by the observed employee/user, or may be sent by an automated contact to an email account or similar method of contacting the user. The system 400 may also tie compliance with host institution protocols to employee compensation or bonuses.

The transmissions of the device over the internet or intranet may be Health Insurance Portability and Accountability Act (HIPAA) compliant and properly encrypted, in healthcare installations. Healthcare host institutions may generate reports, or the like, of use compliance data using the system 400. The reports may be used to negotiate better reimbursement rates from insurers. Healthcare institutions can use compliance data and/or reports to negotiate better premium rates from malpractice liability providers. Healthcare regulatory agencies may use compliance data and/or reports to monitor infections by individuals and on an institution wide basis. Healthcare providers may license this data and/or reports, to demonstrate to patients and other third parties as a quality indicator. All information may be collected by the monitor 404 and/or the system 400 to be analyzed and to facilitate negotiations of savings as contemplated above, and to provide consultations in compliance in healthcare regulatory authorities.

In embodiments of the present invention, the healthcare provider may carry the monitor 404 device, as a modified smart cell phone. The monitor 404 may respond to RFID chips or other unique patient identification as a bar code, QR box or digital fingerprint, and may communicate with other components of the system 400, such as sink timers, soap dispensers, and/or the like. To help prevent spread of infection, the hand held device/smart phone may be surrounded by a shield that interferes with the growth of bacteria. The shield may comprise copper or silver, or the like.

To help prevent spread of infections, hospital apparel that interferes with the growth of bacteria, containing silver or copper or other suitable material, may be provided along with the monitor 404. The monitor 404 and/or the system 400 may collect and provide subscriptions to hand washing data and time data to insurers, so that they can confirm compliance with standard healthcare practices related to services provided to their insured clients. This system can also be used to prevent healthcare fraud and abuse by closer documentation of the performance of procedures.

The monitor 404 may collect and provide documentation of hand hygiene compliance for large customers (hospitals) and for individual users (doctors), which they may use for advertising or promotional activities. The monitor 404 and system 400 may provide infection consulting information and/or the ability to access services for clients. The monitor 404 may provide information and/or the ability to access consulting services in training staff on hand washing techniques.

In one example the monitor 404 may be adapted to monitor compliance with the World Health Organization's (WHO) five moments for hand hygiene. For example, the monitor 404 may be adapted to monitor compliance with the following procedure: before touching a patient, a healthcare worker may be required to pass by a beacon and/or other reader in a room or at the entrance to a ward, to document the first hand hygiene of the work day; a unique identifier may be placed on a kit to be scanned by smart phone app, or the like, before cleaning or aseptic procedures commence.

A unique identifier may be placed inside the kit, or on the back of the kit, or the like, to be scanned at the time of the completion of the procedure. A unique identifier may be placed on patient care items such as intravenous fluid dressings, incontinence briefs or fluid collection bags, to be scanned prior to or after completion of the procedure for the patient. This would allow identification of a moment for hand hygiene at the time of the procedure.

A hand hygiene episode may be required to be recorded before and after a procedure. The hospital can collect this information using the system 400 for audit purposes. Healthcare payors may require this information for payment. For cases done in operating rooms, cards may be prepared and scanned by smart phone app, or the like, by healthcare professionals before and after procedure. Compliance with hand hygiene can be included in the mandated presurgical "time out" or "surgical pause". The hospital may collect this information for audit purposes. Healthcare payors can require this information for payment. For body fluid exposure and risk of exposure, healthcare professionals may use a smart phone app, or the like, to scan a unique identifier on equipment that carries a risk, such as a Foley urine collection bag or a Jackson Pratt drain, or the like. Alternatively, the healthcare worker may scan a unique identifier posted in a room before and after the time of other services, as patient hygiene activities and toileting, or the like. This information can be used as part of quality control, efficiency of service provision, and for disability claims related to exposures to infectious body fluids. For example, if a healthcare worker could not document an exposure to an infected patient, they would not qualify for occupational disability.

After touching a patient, a specific time period, as thirty minutes, could be specified in which, if a healthcare worker, must complete hand hygiene procedures. If that time period expired, a hand hygiene procedure may be required by the system 400. After touching patient surroundings, a healthcare worker may have to "announce" himself or herself by RFID or unique identifier in a room, leading to a need for a hand hygiene event. The healthcare worker may have to signal going to bathroom or leaving immediate patient care activities, as break time or lunch time, triggering the need for another hand hygiene event. For visitors or vendors or other non-patient related hospital visitors, identification badges may be issued, that may trigger beacons, or the like, with audible beeps, or the like, on entering or leaving patient care areas.

Using the monitor 404 and a specific QR box code, bar code, other code, or the like, a healthcare worker may turn off the requirement for a hand hygiene moment when he or she may have walked by a beacon or stood by the opening to a patient room door without entering. Children visitors may have identifications linked to an adult parent or guardian. The adult may have to verify hand hygiene for the child. Access to the system 400 may be restricted by age. Pediatric patients or patients who are impaired and unable to provide for their hand hygiene may have identification linked to that of an adult parent or guardian. Healthcare workers or adults may have to verify hand hygiene for the child or impaired individual.

Figure 5:
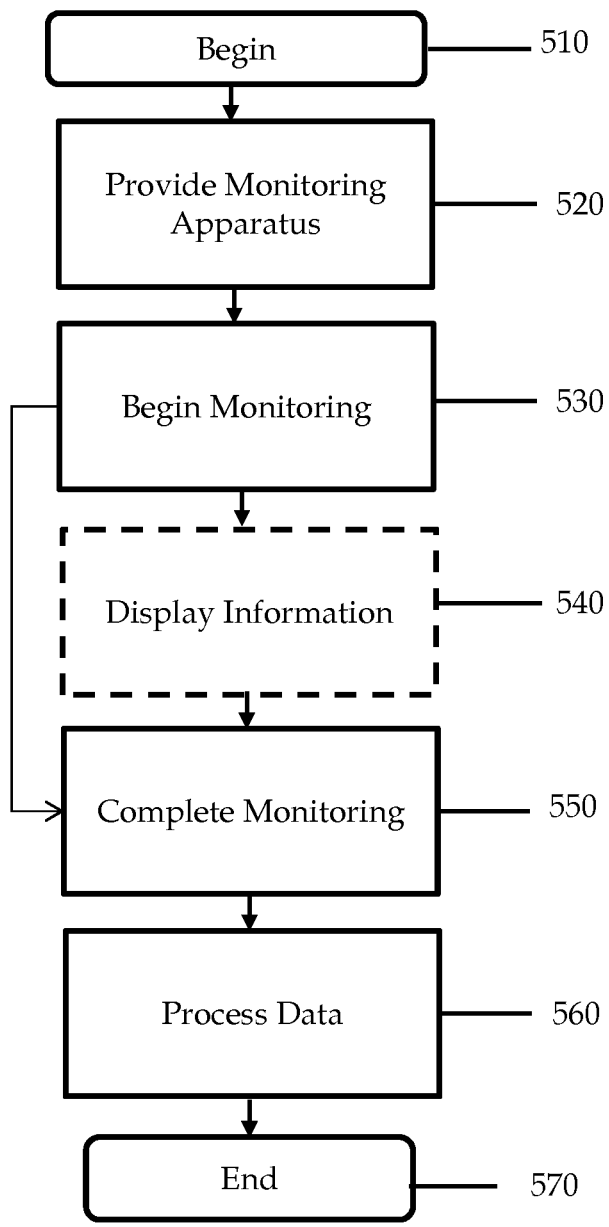
FIG. 5 depicts a flowchart of a method of hygiene monitoring in accordance with exemplary embodiments of the present invention.

FIG. 5 depicts a flowchart of a method of hygiene monitoring in accordance with exemplary embodiments of the present invention. In exemplary embodiments, the computer implemented method 500 may be adapted to capture, transmit, analyze, filter, review, and/or information related to a hygiene process. The method 500 may be carried out using the architecture and components described in the systems above, or may utilize any other type of system architecture suitable for embodiments of the present invention. It should further be appreciated, the steps of method 500 may be carried out in any order (e.g., step 530 may occur before step 520), unless otherwise explicitly specified by the steps of the exemplary method.

For ease, exemplary methods represented in FIG. 4 are described with reference to the client 105, server 115, and system 500 described above. The method 500 may be carried out using other embodiments as well. Many steps of the method 500 may generally be carried out by the system 500. A portion of the system 500 may be stored on a client 105, a server 115, or any other data storage location consistent with the present disclosure. It may be appreciated that the steps of the method 500 may be performed exclusively on the client 105 or partially on the client 105 and partially on the server 115. Any combination of shared computing power for performing the steps of the methods described herein consistent with the present disclosure is contemplated. For example, multiple clients 105 and servers 115 may collaborate to perform the steps of method 500.

The method 500 begins at step 510. At step 520, a monitoring apparatus 404 may be provided. An exemplary monitoring apparatus 404 is described herein with respect to FIG. 4. At step 530, a user may be indetiived by the system 500 and a monitoring process may commence. In some embodiments, the monitoring process may commence when a hygiene process is started. For example, when a sink 402 is turned on, a timer may be started and/or a camera may be activated, or the like. Data may be collected during the hygiene procedure with the monitor 404. The data may be related to a user's compliance with a predetermined hygiene protocol.

At step 540, information, text, video, animation, audio, a presentation, data, and/or the like may be displayed. For example, a countdown timer, a demonstration of a proper hand washing technique, local information, world news, and/or the like may be displayed. In some embodiments, the monitor 404 may not include a display. At step 550, monitoring of the hygiene process/procedure may end. In some embodiments, an indicator, such as a visual or audio indication may signal the end of the monitoring process to the user. At step 560, the monitoring data collected by the monitor 404 may be processed and analyzed by the system 500. In some embodiments, alerts may be generated when a user did not comply with a predetermined hygiene protocol. The alerts may be real-time, accessed on-demand, may be generated at predetermined time intervals, and/or may be indicated on reports generated by the system on predetermined dates. The alerts, or the like, may be printed in a report, displayed on a computer screen via an interface, or the like, transmitted via email, transmitted via text message, and/or stored in a database in accordance with embodiments of the present invention. After the hygiene procedure has concluded, the method 500 ends at step 570.

The monitoring system described herein can be used to document compliance with other issues requiring monitoring that are not related to direct patient care. As examples, the system can monitor employee access to controlled drugs, access to controlled areas of the hospital or other facility, access to hospital equipment that is kept under lock or other controlled access to prevent pilfering or misuse.

While the foregoing is directed to exemplary embodiments of the present disclosure, other and further embodiments of the disclosure may be devised without departing from the basic scope thereof, and should be considered part of this disclosure, as if described fully herein. Specifically, whereas the worldwide web and mobile web are growing content and capabilities at ever-increasing rates, the ability to adapt the systems, methods, applications, and interfaces disclosed herein to existing or new mobile- or web-based technology is contemplated by embodiments of the present disclosure and does not depart the scope of the disclosure disclosed herein.

What is claimed is:

1. A computer-implemented method for monitoring hygiene compliance, the method comprising, at a server having one or more processors and memory storing one or more programs for execution by the one or more processors:

receiving hygiene data from a hygiene monitoring member, the hygiene data indicating the dates and times a user used a hygiene improvement apparatus and the length of time the user used the hygiene improvement apparatus, wherein the hygiene improvement apparatus is a standard sink for washing the hands of a user, and wherein the hygiene monitoring member is adapted to be used with a standard sink;

comparing the hygiene data with a hygiene protocol;

determining if the hygiene data conforms to the hygiene protocol;

generating an alert if the hygiene data does not comply with the hygiene protocol; and storing the hygiene data in a database;

saving the alert in the database;

transmitting an indication that an infection is related to the failure of the user to comply with the hygiene protocol if any incidents of infection occur in people the user interacts with during a specified time after the generation of the alert;

wherein the hygiene protocol requires that the user wash their hands for at least twenty seconds per hand washing session;

wherein the hygiene monitor comprises a countdown timer that is activated when the hygiene improvement apparatus is turned on;

wherein the hygiene monitor is adapted to display an indication of an amount of time remaining to comply with the hygiene protocol; and wherein the hygiene monitor is adapted to provide at least one of an audio signal and a visual signal when the amount of time remaining is zero.

2. The method of claim 1, wherein the hygiene monitor is adapted to identify the user with a unique identifier.

3. The method of claim 2, wherein the unique identifier comprises at least one of an identifying code, a bar code, a radio-frequency identification tag, and a fingerprint.

4. The method of claim 2, further comprising displaying at least one of a targeted advertisement, news content, educational content, and entertainment content to the user based on settings associated with the user.

5. The method of claim 1, wherein the hygiene monitor is adapted to display a video demonstration of a hand washing method in compliance with the hygiene protocol.

6. The method of claim 1, wherein the hygiene monitor is integral with a soap dispenser.

7. The method of claim 1, further comprising generating a report listing the user that is not in compliance with the hygiene protocol within a time period.

8. The method of claim 1, further comprising allocating a reward to the user if the user is in compliance with the hygiene protocol.

9. A system comprising at least one client, the client comprising:

one or more processors; and memory;

wherein the at least one client is adapted to:

collect hygiene data indicating the dates and times a user used a hygiene improvement apparatus and the length of time the user used the hygiene improvement apparatus, wherein the hygiene improvement apparatus is a standard sink for washing the hands of a user, and wherein the client is adapted to be used with a standard sink;

compare the hygiene data with a hygiene protocol;

determine if the hygiene data conforms to the hygiene protocol;

generate an alert if the hygiene data does not conform to the hygiene protocol; and transmit hygiene data to a server for storage on a database;

wherein the client requires that the user wash their hands for at least twenty seconds per hand washing session.;

wherein the client comprises a countdown timer that is activated when the hygiene improvement apparatus is turned on;

wherein the client is adapted to display an indication of an amount of time remaining to comply with the hygiene protocol; and wherein the client is adapted to provide at least one of an audio signal and a visual signal when the amount of time remaining is zero.

10. The system of claim 9, wherein the client is adapted to identify the user with a unique identifier, the unique identifier comprising at least one of an identifying code, a bar code, a radio-frequency identification tag, and a fingerprint.

11. The system of claim 9, wherein the client is adapted to display at least one of targeted advertisements, local news, educational content, and entertainment content to the user based on settings associated with the user.

* * * * *